(12) United States Patent
Manzer et al.

(10) Patent No.: US 6,476,085 B2
(45) Date of Patent: Nov. 5, 2002

(54) FISCHER-TROPSCH PROCESSES USING CATALYSTS ON MESOPOROUS SUPPORTS

(75) Inventors: Leo E. Manzer, Wilmington, DE (US); Stephan Schwarz, Wilmington, DE (US)

(73) Assignee: Conoco Inc., Houston, TX (US)

( * ) Notice: Subject to any disclaimer, the term of this patent is extended or adjusted under 35 U.S.C. 154(b) by 0 days.

(21) Appl. No.: 09/990,812

(22) Filed: Nov. 16, 2001

(65) Prior Publication Data

US 2002/0052289 A1 May 2, 2002

Related U.S. Application Data

(62) Division of application No. 09/376,873, filed on Aug. 18, 1999, now Pat. No. 6,319,872.
(60) Provisional application No. 60/097,192, filed on Aug. 20, 1998, provisional application No. 60/097,193, filed on Aug. 20, 1998, and provisional application No. 60/097,194, filed on Aug. 20, 1998.

(51) Int. Cl.[7] ............................ C07C 27/00; B01J 29/06; B01J 21/00; B01J 29/04
(52) U.S. Cl. .................... 518/715; 518/700; 502/60; 502/66; 502/74; 502/87
(58) Field of Search ................... 518/700, 715; 502/60, 66, 87, 74

(56) References Cited

U.S. PATENT DOCUMENTS

| | | | |
|---|---|---|---|
| 5,028,634 A | 7/1991 | Fiato | 518/707 |
| 5,110,572 A | 5/1992 | Calabro et al. | 423/328 |
| 5,156,828 A | 10/1992 | Degnan et al. | 423/709 |
| 5,211,934 A | 5/1993 | Kresge et al. | 423/706 |
| 5,215,737 A | 6/1993 | Chu et al. | 423/706 |
| 5,227,353 A | 7/1993 | Apelian et al. | 502/74 |
| 5,238,676 A | 8/1993 | Roth et al. | 423/713 |
| 5,302,622 A | 4/1994 | Chaumette et al. | 518/713 |
| 5,366,945 A | 11/1994 | Kresge et al. | 502/60 |
| 5,368,835 A | 11/1994 | Choudhary et al. | 423/651 |
| 5,399,537 A | 3/1995 | Bhattacharyya et al. | 502/84 |
| 5,411,927 A | 5/1995 | Choudhary et al. | 502/302 |
| 5,431,855 A | 7/1995 | Green et al. | 252/373 |
| 5,439,861 A | 8/1995 | Bhattacharyya et al. | 502/84 |
| 5,447,705 A | 9/1995 | Petit et al. | 423/418.2 |
| 5,500,149 A | 3/1996 | Green et al. | 252/373 |
| 5,506,272 A | 4/1996 | Benham et al. | 518/700 |
| 5,591,238 A | 1/1997 | Bhattacharyya et al. | 48/198.7 |
| 5,614,163 A | 3/1997 | Bhatttacharyya et al. | 423/418.2 |
| 5,639,401 A | 6/1997 | Jacobs et al. | 252/373 |
| 5,652,193 A | 7/1997 | Herskowitz | 502/332 |

FOREIGN PATENT DOCUMENTS

| | | | |
|---|---|---|---|
| EP | 0629578 | 12/1994 | |
| EP | 0911079 A2 | 4/1999 | B01J/31/22 |
| GB | 2239406 | 7/1991 | |
| GB | 2085314 | 4/1992 | |
| WO | WO9211199 | 7/1992 | |
| WO | WO93/91884 | 2/1993 | B01J/29/06 |
| WO | WO9414700 | 7/1994 | |
| WO | 9604200 | 2/1996 | |
| WO | WO00/73205 A1 | 12/2000 | C01B/31/02 |

OTHER PUBLICATIONS

International Search Report dated Jul. 7, 2000 for International Application No. PCT/US99/18994.
J. S. Beck, et al; *A New Family of Mesoporous Molecular Sieves Prepared with Liquid Crystal Templates*; J. Am. Chem. Soc. 1992, vol. 114, (pp. 10834–43).
C. T. Kresge, et al; *Ordered Mesoporous Molecular Sieves Synthesized by a Liquid–Crystal Template Mechanism*; Letters to Nature, vol. 359, Oct. 22, 1992, (pp. 710–12).
P. T. Tanev, et al; *A Neutral Templating Route to Mesoporous Molecular Sieves*; Science, vol. 267, Feb. 10, 1995; (pp. 865–867).
G. S. Attard, *Liquid–Crystalline Phases as Templates for the Synthesis of Mesoporous Silica*; Letters to Nature, vol. 378, Nov. 23, 1995; (pp. 366–368).
Q. Huo, et al; *Surface Control of Phases in the Synthesis of Mesoporous Silica–Based Materials*; Chem. Mater., vol. 8, No. 5,, Nov. 5, 1996; (pp. 1147–1160.

*Primary Examiner*—Jafar Parsa
(74) *Attorney, Agent, or Firm*—Conley, Rose & Tayon PC

(57) ABSTRACT

This invention provides a process for producing hydrocarbons. The process involves contacting a feed stream comprising hydrogen and carbon monoxide with a catalyst in a reaction zone maintained at conversion-promoting conditions effective to produce an effluent stream comprising hydrocarbons, and uses a catalyst including (a) at least one catalytic metal for Fischer-Tropsch reactions (e.g., iron, cobalt, nickel and/or ruthenium) and (b) a non-layered mesoporous support which exhibits an X-ray diffraction after calcination that has at least one peak at a d-spacing of greater than 18 Ångstrom units.

6 Claims, No Drawings

FISCHER-TROPSCH PROCESSES USING CATALYSTS ON MESOPOROUS SUPPORTS

CROSS-REFERENCE TO RELATED APPLICATIONS

This application claims the benefit of U.S. provisional patent application Serial No. 60/097,192, filed Aug. 20, 1998, U.S. provisional patent application Serial No. 60/097,193, filed Aug. 20, 1998, U.S. provisional patent application Serial No. 60/097,194, filed Aug. 20, 1998, and divisional of Ser. No. 09/376,873, filed Aug. 18, 1999 U.S. Pat. No. 6,319,872 all of which are incorporated herein by reference in their entirety.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, (i.e., a mixture of carbon monoxide and hydrogen), typically labeled the Fischer-Tropsch process. Particularly, this invention relates to supported catalysts containing metals on mesoporous materials.

BACKGROUND OF THE INVENTION

Large quantities of methane, the main component of natural gas, are available in many areas of the world. Methane can be used as a starting material for the production of hydrocarbons. The conversion of methane to hydrocarbons is typically carried out in two steps. In the first step methane is reformed with water or partially oxidized with oxygen to produce carbon monoxide and hydrogen (i.e., synthesis gas or syngas). In a second step, the syngas is converted to hydrocarbons.

The preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active Group VIII (CAS) metal. In particular, iron, cobalt, nickel, and ruthenium have been abundantly used as the catalytically active metals. Cobalt and ruthenium have been found to be most suitable for catalyzing a process in which synthesis gas is converted to primarily hydrocarbons having five or more carbon atoms (i.e., where the $C_5^+$ selectivity of the catalyst is high). Additionally, the catalysts often contain one or more promoters and a support or carrier material. Rhenium is a widely used promoter.

The Fischer-Tropsch reaction involves the catalytic hydrogenation of carbon monoxide to produce a variety of products ranging from methane to higher aliphatic alcohols. The methanation reaction was first described in the early 1900's, and the later work by Fischer and Tropsch dealing with higher hydrocarbon synthesis was described in the 1920's.

The Fischer-Tropsch synthesis reactions are highly exothermic and reaction vessels must be designed for adequate heat exchange capacity. Because the feed streams to Fischer-Tropsch reaction vessels are gases while the product streams include liquids, the reaction vessels must have the ability to continuously produce and remove the desired range of liquid hydrocarbon products. The process has been considered for the conversion of carbonaceous feedstock, e.g., coal or natural gas, to higher value liquid fuel or petrochemicals. The first major commercial use of the Fischer-Tropsch process was in Germany during the 1930's. More than 10,000 B/D (barrels per day) of products were manufactured with a cobalt based catalyst in a fixed-bed reactor. This work has been described by Fischer and Pichler in Ger. Pat. No. 731,295 issued Aug. 2, 1936.

Motivated by production of high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Tex., using powdered iron as the catalyst. Due to disappointing levels of conversion, scale-up problems, and rising natural gas prices, operations at this plant were suspended in 1957. Research has continued, however, on developing Fischer-Tropsch reactors such as slurry-bubble columns, as disclosed in U.S. Pat. No. 5,348,982 issued Sep. 20, 1994.

Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research is likewise continuing on the development of more efficient Fischer-Tropsch catalyst systems and reaction systems that increase the selectivity for high-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution or product selectivity depends heavily on the type and structure of the catalysts and on the reactor type and operating conditions. Accordingly, it is highly desirable to maximize the selectivity of the Fischer-Tropsch synthesis to the production of high-value liquid hydrocarbons, such as hydrocarbons with five or more carbon atoms per hydrocarbon chain.

U.S. Pat. No. 4,659,681 issued on Apr. 21, 1987, describes the laser synthesis of iron based catalyst particles in the 1–100 micron particle size range for use in a slurry reactor for Fischer-Tropsch synthesis.

U.S. Pat. No. 4,619,910 issued on Oct. 28, 1986, U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure. The catalysts are activated in a fixed-bed reactor by reaction with $CO+H_2$ prior to slurrying in the oil phase in the absence of air.

Catalyst supports for catalysts used in Fischer-Tropsch synthesis of hydrocarbons have typically been oxides (e.g., silica, alumina, titania, zirconia or mixtures thereof, such as silica-alumina). It has been claimed that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). The products prepared by using these catalysts usually have a very wide range of molecular weights.

U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst. U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group IIIA or Group IVB metal oxide, e.g., thoria. European Patent No. 142,887 discloses a silica supported cobalt catalyst together with zirconium, titanium, ruthenium and/or chromium.

U.S. Pat. No. 4,801,573 discloses a promoted cobalt and rhenium catalyst, preferably supported on alumina that is characterized by low acidity, high surface area, and high purity, which properties are said to be necessary for high activity, low deactivation, and high molecular weight products. The amount of cobalt is most preferably about 10 to 40 wt % of the catalyst. The content of rhenium is most preferably about 2 to 20 wt % of the cobalt content. Related U.S. Pat. No. 4,857,559 discloses a catalyst most preferably having 10 to 45 wt % cobalt and a rhenium content of about 2 to 20 wt % of the cobalt content. In both of the above patents the method of depositing the active metals and promoter on the alumina support is described as not critical.

U.S. Pat. No. 5,545,674 discloses a cobalt-based catalyst wherein the active metal is dispersed as a very thin film on the surface of a particulate support, preferably silica or titania or a titania-containing support. The catalyst may be prepared by spray techniques.

U.S. Pat. No. 5,028,634 discloses supported cobalt-based catalysts, preferably supported on high surface area aluminas. High surface area supports are said to be preferred because greater cobalt dispersion can be achieved as cobalt is added, with less tendency for one crystal of cobalt to fall on another crystal of cobalt. The cobalt loading on a titania support is preferably 10 to 25 wt %, while the preferred cobalt loading on an alumina support is 5 to 45 wt %.

International Publication Nos. WO 98/47618 and WO 98/47620 disclose the use of rhenium promoters and describe several functions served by the rhenium.

U.S. Pat. No. 5,248,701 discloses a copper promoted cobalt-manganese spinel that is said to be useful as a Fischer-Tropsch catalyst with selectivity for olefins and higher paraffins. U.S. Pat. No. 5,302,622 discloses a supported cobalt and ruthenium based catalyst including other components and preferably prepared by a gelling procedure to incorporate the catalyst components in an alcogel formed from a hydrolyzable compound of silicon, and/or aluminum, and optional compounds. The cobalt content after calcination is preferably between 14 and 40 wt % of the catalyst.

UK Patent Application GB 2,258,414A, published Feb. 10, 1993, discloses a supported catalyst containing cobalt, molybdenum and/or tungsten, and an additional element. The support is preferably one or more oxides of the elements Si, Al, Ti, Zr, Sn, Zn, Mg, and elements with atomic numbers from 57 to 71. After calcination, the preferred cobalt content is from 5 to 40 wt % of the catalyst. A preferred method of preparation of the catalyst includes the preparation of a gel containing the cobalt and other elements.

A gel may be described as a coherent, rigid three-dimensional polymeric network. The present gels are formed in a liquid medium, usually water, alcohol, or a mixture thereof. The term "alcogel" describes gels in which the pores are filled with predominantly alcohol. Gels whose pores are filled primarily with water may be referred to as aquagels or hydrogels.

A "xerogel" is a gel from which the liquid medium has been removed and replaced by a gas. In general, the structure is compressed and the porosity reduced significantly by the surface tension forces that occur as the liquid is removed. As soon as liquid begins to evaporate from a gel at temperatures below the critical temperature, surface tension creates concave menisci in the gel's pores. As evaporation continues, the menisci retreat into the gel body, compressive forces build up around its perimeter, and the perimeter contracts, drawing the gel body inward. Eventually surface tension causes significant collapse of the gel body and a reduction of volume, often as much as two-thirds or more of the original volume. This shrinkage causes a significant reduction in the porosity, often as much as 90 to 95 percent depending on the system and pore sizes.

In contrast, an "aerogel" is a gel from which the liquid has been removed in such a way as to prevent significant collapse or change in the structure as liquid is removed. This is typically accomplished by heating the liquid-filled gel in an autoclave while maintaining the prevailing pressure above the vapor pressure of the liquid until the critical temperature of the liquid has been exceeded, and then gradually releasing the vapor, usually by gradually reducing the pressure either incrementally or continuously, while maintaining the temperature above the critical temperature. The critical temperature is the temperature above which it is impossible to liquefy a gas, regardless of how much pressure is applied. At temperatures above the critical temperature, the distinction between liquid and gas phases disappears and so do the physical manifestations of the gas/liquid interface. In the absence of an interface between liquid and gas phases, there is no surface tension and hence no surface tension forces to collapse the gel. Such a process may be termed "supercritical drying." Aerogels produced by supercritical drying typically have high porosities, on the order of from 50 to 99 percent by volume.

International Publication No. WO 96/19289 discloses active metal coated catalysts supported on an inorganic oxide, and notes that dispersion of the active metal on Fischer-Tropsch catalysts has essential effects on the activity of the catalyst and on the composition of the hydrocarbons obtained.

Despite the vast amount of research effort in this field, there is still a great need for new catalysts for Fischer-Tropsch synthesis, particularly catalysts that provide high $C_5^+$ hydrocarbon selectivities to maximize the value of the hydrocarbons produced and thus enhance the process economics.

SUMMARY OF THE INVENTION

This invention provides a process for producing hydrocarbons. The process comprises contacting a feed stream comprising hydrogen and carbon monoxide with a catalyst in a reaction zone maintained at conversion-promoting conditions effective to produce an effluent stream comprising hydrocarbons. In accordance with this invention the catalyst used in the process comprises (a) at least one catalytic metal for Fischer-Tropsch reactions (e.g., at least one metal selected from the group consisting of iron, cobalt, nickel and ruthenium); and (b) a non-layered mesoporous support which exhibits an X-ray diffraction after calcination that has at least one peak at a d-spacing of greater than 18 Angstrom units.

In accordance with this invention, the catalyst used in the process comprises a catalytically active metal selected from the group consisting of iron, cobalt, nickel, ruthenium, and combinations thereof, a support material comprising an inorganic, non-layered mesoporous crystalline phase with a composition represented by $M_{n/q}(W_aX_bY_cZ_dO_h)$ where M is at least one ion selected from the group consisting of ammonium, sodium, potassium, and hydrogen, n is the charge of the composition excluding M expressed as oxides, q is the weighted molar average valence of M, n/q is the mole fraction of M, W is at least one divalent element, X is at least one trivalent element, Y is at least one tetravalent element, Z is at least one pentavalent, a, b, c, and d are mole fractions of W, X, Y and Z, respectively, h is a number from 1 to 2.5, and (a+b+c+d)=1.

This invention also includes a Fischer-Tropsch catalyst comprising at least one catalytically active metal and a non-layered mesoporous support that exhibits an X-ray diffraction pattern after calcination that has at least one peak at a d-spacing of greater than 18 Ångstrom units.

This invention also includes a method for the preparation of a Fischer-Tropsch catalyst comprising impregnating a support with a salt of a catalytically active metal selected from the group consisting of iron, cobalt, nickel, ruthenium, and combinations thereof, wherein the support comprises a non-layered mesoporous support that exhibits an X-ray diffraction pattern after calcination that has at least one peak at a d-spacing of greater than 18 Ångstrom units, and drying the impregnated support.

DETAILED DESCRIPTION OF THE INVENTION

The feed gases charged to the process of the invention comprise hydrogen, or a hydrogen source, and carbon monoxide. $H_2/CO$ mixtures suitable as a feedstock for conversion to hydrocarbons according to the process of this invention can be obtained from light hydrocarbons such as methane by means of steam reforming, partial oxidation, or other processes known in the art. The hydrogen is preferably provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). When cobalt, nickel, and/or ruthenium catalysts are used, the feed gas stream preferably contains hydrogen and carbon monoxide in a molar ratio of about 2:1. When iron catalysts are used, the feed gas stream preferably contains hydrogen and carbon monoxide in a molar ratio of about 0.67:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds, such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column or ebullating bed reactors, among others, may be used. Accordingly, the size and physical form of the catalyst particles may vary depending on the reactor in which they are to be used.

A component of the catalysts used in this invention is the support material (b) which carries the active catalyst component (a). Typically, the support material contains an inorganic, non-layered mesoporous crystalline phase with a composition of the formula: $M_{n/q}(W_aX_bY_cZ_dO_h)$ where M is one or more ions such as ammonium, sodium, potassium and/or hydrogen; n is the charge of the composition excluding M expressed as oxides; q is the weighted molar average valence of M; n/q is the number of moles or mole fraction of M; W is one or more divalent elements such as a divalent first row transition metal, (e.g., manganese, iron and cobalt) and/or magnesium, preferably cobalt; X is one or more trivalent elements such as aluminum, boron, iron and/or gallium, preferably aluminum; Y is one or more tetravalent elements (e.g., titanium, zirconium, hafnium, manganese, silicon and/or germanium), preferably silicon; Z is one or more pentavalent elements (e.g., niobium, tantalum, vanadium and phosphorus) preferably phosphorus; a, b, c, and d are mole fractions of W, X, Y and Z, respectively; h is a number from 1 to 2.5; and (a+b+c+d)=1.

A preferred embodiment of the above composition is where the sum (a+b+c) is greater than d, and h is 2. A further embodiment is when a and d are 0, and h is 2.

Also preferred are compositions where (a+b+c) is less than d and h is 2.5 and Z is niobium or tantalum (e.g., $Nb_2O_5$ and $Ta_2O_5$).

Further details about the preparation and characterization of the above-described inorganic, non-layered mesoporous crystalline phase compositions are described in U.S. Pat. No. 5,232,580 which is incorporated by reference herein in its entirety. Descriptions of mesoporous molecular sieve materials and their use in catalysis can be found in A. Corma, Chem. Rev. (1997), 97, 2373–2419, hereby incorporated herein by reference in its entirety.

The silica-based mesoporous M415 molecular sieves are preferred in the preparation of the catalysts of the present invention. These include Si-MCM-41 and Al-MCM-41, where Si-MCM-41 refers to purely siliceous MCM-41 and Al-MCM-41 refers to MCM-41 where some Si atoms have been replaced by Al atoms.

Another component of the catalyst of the present invention is the catalytic metal. The catalytic metal is preferably selected from iron, cobalt, nickel and/or ruthenium. Normally, the metal component on the support is reduced to provide elemental metal (e.g., elemental iron, cobalt, nickel and/or ruthenium) before use. The catalyst contains a catalytically effective amount of the metal component(s). The amount of catalytic metal present in the catalyst may vary widely. Typically, the catalyst comprises about 1 to 50% by weight (as the metal) of total supported iron, cobalt, nickel and/or ruthenium per total weight of catalytic metal and support, preferably, about 1 to 30% by weight.

Each of the metals can be used individually or in combination with other metals, especially cobalt and ruthenium, cobalt and rhenium, and cobalt and platinum. Preferred are catalysts comprising from about 10 to 30% by weight of a combination of cobalt and ruthenium where the ruthenium content is from about 0.001 to about 1 weight %.

Optionally, the catalyst may comprise one or more additional promoters or modifiers known to those skilled in the art. When the catalytic metal is iron, cobalt, nickel and/or ruthenium, suitable promoters include at least one metal selected from the group consisting of Group IA (CAS) metals (i.e., Na, K, Rb, Cs), Group IIA metals (i.e., Mg, Ca, Sr, Ba), Group IB metals (i.e., Cu, Ag, and Au), Group IIIB metals (i.e., Sc, Y and La), Group IVB metals (i.e., Ti, Zr and Hf), Group VB metals (i.e., V, Nb and Ta), and Rh, Pd, Os, Ir, Pt, Mn, B, P, and Re. Preferably, any additional promoters for the cobalt and/or ruthenium are selected from Sc, Y and La, Ti, Zr, Hf, Rh, Pd, Os, Ir, Pt, Re, Nb, Cu, Ag, Mn, B, P, and Ta. Preferably, any additional promoters for the iron catalysts are selected from Na, K, Rb, Cs, Mg, Ca, Sr and Ba. The amount of additional promoter, if present, is typically between 0.001 and 40 parts by weight per 100 parts of the support or carrier. Combinations of cobalt and rhenium and combinations of cobalt and platinum are preferred. More preferred are catalysts comprising from about 10 to 30% by weight of a combination of cobalt and rhenium, where the rhenium content is from about 0.001 to about 1 weight %; and catalysts comprising from about 10 to 30% of a combination of cobalt and platinum where the platinum content is from about 0.001 to 1 weight %.

The catalysts of the present invention may be prepared by methods known to those skilled in the art. These include impregnating the catalytically active compounds or precursors onto a support, extruding one or more catalytically active compounds or precursors together with support material to prepare catalyst extrudates and spray-drying the supported catalytically active compounds. Accordingly, the supported catalysts of the present invention may be used in the form of powders, particles, pellets, monoliths, honeycombs, packed beds, foams, and aerogels.

The most preferred method of preparation may vary among those skilled in the art, depending for example on the desired catalyst particle size. Those skilled in the art are able to select the most suitable method for a given set of requirements.

One method of preparing a supported metal catalyst (e.g., a supported cobalt catalyst) is by incipient wetness impregnation of the support with an aqueous solution of a soluble metal salt such as nitrate, acetate, acetylacetonate or the like. Another method involves preparing the catalyst from a molten metal salt. For example, the support can be impregnated with a molten metal nitrate (e.g., $Co(NO_3)_2 \cdot 6H_2O$). Alternatively, the support can be impregnated with a solution of zero valent cobalt such as $Co_2(CO)_8$, $Co_4(CO)_{12}$ or the like in a suitable organic solvent (e.g., toluene). The impregnated support is dried and reduced with hydrogen. The hydrogen reduction step may not be necessary if the catalyst is prepared with zero valent cobalt. In another embodiment, the impregnated support is dried, oxidized with air or oxygen and reduced with hydrogen.

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as well as a mixture of hydrogen and an inert gas such as nitrogen. The amount of hydrogen may range from about 1% to about 100% by volume.

The Fischer-Tropsch process is typically run in a continuous mode. In this mode, the gas hourly space velocity through the reaction zone typically may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), and still more preferably, from about 140 psig (1066 kPa) to about 400 psig (2858 kPa).

The products resulting from the process will have a great range of molecular weights. Typically, the carbon number range of the product hydrocarbons will start at methane and continue to the limits observable by modern analysis, about 50 to 100 carbons per molecule. The process is particularly useful for making hydrocarbons having five or more carbon atoms, especially when the above-referenced preferred space velocity, temperature and pressure ranges are employed.

The wide range of hydrocarbons produced in the reaction zone will typically afford liquid phase products at the reaction zone operating conditions. Therefore the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone, together with any liquid from a subsequent separation zone, may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following embodiments are to be construed as illustrative, and not as constraining the scope of the present invention in any way whatsoever.

EXAMPLES

General Procedure For Batch Tests

Each of the catalyst samples was treated with hydrogen prior to use in the Fischer-Tropsch reaction. The catalyst sample was placed in a small quartz crucible in a chamber and purged with 500 sccm ($8.3 \times 10^{-6}$ m$^3$/s) nitrogen at room temperature for 15 minutes. The sample was then heated under 100 sccm ($1.7 \times 10^{-6}$ m$^3$/s) hydrogen at 1° C./minute to 100° C. and held at 100° C. for one hour. The catalysts were then heated at 1° C./minute to 400° C. and held at 400° C. for four hours under 100 sccm ($1.7 \times 10^{-6}$ m$^3$/s) hydrogen. The samples were cooled in hydrogen and purged with nitrogen before use. Examples 9 and 10 were heat treated under helium as described in the specific examples.

A 2 mL pressure vessel was heated at 225° C. under 1000 psig (6994 kPa) of $H_2$:CO (2:1) and maintained at that temperature and pressure for 1 hour. In a typical run, roughly 50 mg of the hydrogen catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of $C_{11}$–$C_{40}$ were analyzed relative to the internal standard. The lower hydrocarbons were not analyzed since they are masked by the solvent and are also vented as the pressure is reduced.

A $C_{11}^+$ Productivity (g $C_{11}^+$/hour/kg catalyst) was calculated based on the integrated production of the $C_{11}$–$C_{40}$ hydrocarbons per kg of catalyst per hour. The logarithm of the weight fraction for each carbon number $\ln(W_n/n)$ was plotted as the ordinate vs. number of carbon atoms in $(W_n/n)$ as the abscissa. From the slope, a value of alpha was obtained. Some runs displayed a double alpha as shown in the tables. The results of runs over a variety of catalysts at 225° C. are shown in Table 1.

Support Preparation

A. Si-MCM-41

A stiff homogeneous gel was prepared by shaking Aerosil™ 200 $SiO_2$ (20 g), $H_2O$ (95.4 g) and a 50% NaOH solution (9.07 g) in a 500 mL polyolefin bottle. A solution of dodecyltrimethylammonium bromide (51.39 g) in $H_2O$ (80.1 g) was added to the polyolefin bottle, and the contents of the closed bottle were stirred with a magnetic stirrer for 1 hour. Shaking may be necessary to start the stirring. The product gel was poured into a Teflon® (polytetrafluoroethylene) bottle; the bottle was sealed and put into an oven at 95° C. for 5 days. The solids were filtered, washed with hot water until foaming stopped and dried. The solids were then calcined in air at the following according to the following schedule rates: from room temperature to 110° C. at 10° C./min.; from 110° C. to 200° C. at 5° C./min.; and finally from 200° C. to 550° C. at 1° C./min., where it was held for 4 hours before cooling to room temperature. An X-ray diffraction pattern of a sample of the recovered calcined solids showed it to have the MCM-41 structure with a peak at a d-spacing of 38 Ångstroms. The Si-MCM-41 was used to prepare the catalyst described in Examples 1 to 9.

B. Al-MCM-41

A thin suspension of Aerosil™ 200 $SiO_2$ (10.1 g), $H_2O$ (40 g) and tetramethylammoniumhydroxide (5.36 g, 25% in $H_2O$) was prepared in a polyolefin bottle. The suspension was stirred for 20 minutes. To a solution of cetyltrimethylammoniumbromide (18.98 g), $H_2O$ (144.4 g) and a 50% in $H_2O$ NaOH solution (2.34 g) prepared by warming in a water-bath was added the $SiO_2$ suspension and stirred for 20 minutes. Aluminum isopropoxide (1.357 g) was added to the suspension and stirring was maintained for 12 minutes. The product was poured into a Teflon® (polytetrafluoroethylene) bottle; the bottle was sealed and put into an oven at 100° C. for 3 days and 3 hours. The solids were filtered, washed with hot deionized water (3 L) and vacuum dried. The solids were then calcined in air at the following rates: from room temperature to 110° C. at 10° C./min.; from 110° C. to 200° C. at 5° C./min.; and finally from 200° C. to 550° C. at 1° C./min., where it was held for 4 hours before cooling to room temperature. An X-ray diffraction pattern of a sample of the recovered calcined solids showed it to have the MCM-41, with a peak at a d-spacing of 29 Ångstroms. The Al-MCM-42 was used to prepare the catalyst described in Example 10.

Catalyst Synthesis

Example 1

Si-MCM-41 (2 g) was slurried with an aqueous solution of $RuCl_3$ (0.2 g) in a rotary evaporator. The water was removed under vacuum at 70° C. The dried material was calcined at 250° C. under 1500 cc/minute of air.

The catalyst had a nominal composition of 5 wt. % Ru on Si-MCM-41.

Example 2

Si-MCM-41 (1.8 g) was slurried with an aqueous solution of $RuCl_3$ (0.36 g) in a rotary evaporator. The water was removed under vacuum at 70° C. The dried material was calcined at 250° C. under 1500 cc/minute of air.

The catalyst had a nominal composition of 10 wt. % Ru/Si-MCM-41.

Example 3

Si-MCM-41 (2 g) was slurried with an aqueous solution of $Co(NO_3)_2 \cdot 6H_2O$ (1.6 g) in a rotary evaporator. The water was removed under vacuum at 70° C. The dried material was calcined at 250° C. under 1500 cc/minute of air. This material was slurried with an aqueous solution of $Co(NO_3)_2 \cdot 6H_2O$ (1.4 g) and $Pt(NH_3)_4(NO_3)_2$ (2.5 mg) in a rotary evaporator. The water was removed under vacuum at 70° C. The dried material was calcined at 250° C. under 1500 cc/minute of air.

The catalyst had a nominal composition of 25 wt. % Co/0.08 wt. % Pt/Si-MCM-41.

Example 4

Si-MCM-41 (2 g) was slurried with an aqueous solution of $Pt(NH_3)_4(NO_3)_2$ (2.5 mg). The water was removed under vacuum at 70° C. This material was slurried with an aqueous solution of $Co(NO_3)_2 \cdot 6H_2O$ (1.6 g) in a rotary evaporator. The water was removed under vacuum at 70° C. The dried material was calcined at 250° C. under 1500 cc/minute of air. This material was slurried with an aqueous solution of 1.4 g $Co(NO_3)_2 \cdot 6H_2O$ and in a rotary evaporator. The water was removed under vacuum at 70° C. The dried material was calcined at 250° C. under 1500 cc/minute of air.

The catalyst had a nominal composition of 25 wt. % Co/0.05 wt. % Pt/Si-MCM-41.

Example 5

Si-MCM-41 (1.5 g) was slurried with an aqueous solution of $Co(CH_3COO)_2 \cdot 4H_2O$ (0.95 g) in a rotary evaporator. The water was removed under vacuum at 70° C. The dried material was calcined at 250° C. under 1500 cc/minute of air. This material is designated Example 5A. A portion of this material (0.65 g) was slurried with an acetone solution of $Co(CH_3COO)_2 \cdot 4H_2O$ (0.4 g) and ruthenium acetylacetonate (3 mg, Ruacac₃) in a rotary evaporator. The acetone was removed under vacuum at 70° C. The dried material was calcined at 250° C. under 1500 cc/minute of air.

The catalyst had a nominal composition of 25 wt. % Co/0.1 wt. % Ru/Si-MCM-41.

Example 6

Si-MCM-41 (1.5 g) was slurried with an aqueous solution of $Co(NO_3)_2 \cdot 6H_2O$ (1.2 g) in a rotary evaporator. The water was removed under vacuum at 70° C. The dried material was calcined at 250° C. under 1500 cc/minute of air. This material is designated Example 6B. A portion of this material (0.85 g) was slurried with an acetone solution of $Co(NO_3)_2 \cdot 6H_2O$ (0.60 g) and Ruacac₃ (4 mg) in a rotary evaporator. The acetone was removed under vacuum at 70° C. The dried material was calcined at 250° C. under 1500 cc/minute of air.

The catalyst had a nominal composition of 25 wt. % Co/0.1 wt. % Ru/Si-MCM-41.

Example 7

Example 5A material (0.65 g) was slurried with an aqueous solution of Co(CH$_3$COO)$_2$.4H$_2$O (0.4 g) and RuCl$_3$ (1.5 mg) in a rotary evaporator. The water was removed under vacuum at 70° C. The dried material was calcined at 250° C. under 1500 cc/minute of air.

The catalyst had a nominal composition of 25 wt. % Co/0.1 wt. % Ru/Si-MCM-41.

Example 8

Example 6B material (0.9 g) was slurried with an aqueous solution of Co(NO$_3$)$_2$.6H$_2$O (0.635 g) and RuCl$_3$ (2 mg) in a rotary evaporator. The water was removed under vacuum at 70° C. The dried material was calcined at 250° C. under 1500 cc/minute of air.

The catalyst had a nominal composition of 25 wt. % Co/0.1 wt. % Ru/Si-MCM-41.

Example 9

Si-MCM)-41 was dried at 200° C. for 30 minutes under flowing N$_2$. It was then mixed thoroughly with Co$_2$(CO)$_8$ (0.2 g) in a glove box. This mixture of solids was placed into a tube furnace boat in a sealed tube and removed from the glove box. It was then heated in a flow of He at 100° C. for 15 minutes, raised to 200° C. over 10 minutes, then heated at 200° C. in He for 30 minutes.

The catalyst had a nominal composition of 16 wt. % Co/Si-MCM-41.

Example 10

The procedure was identical to that of Example 9 except that the support was Al-MCM-41.

The catalyst had a nominal composition of 16 wt. % Co/Al-MCM-41.

TABLE 1

(225° C.)

| Ex. No. | Catalyst | C$_{11}$ + Productivity | Alpha |
|---|---|---|---|
| 1 | Ru(5)/Si-MCM-41 | 17 | 0.87 |
| 2 | Ru(10)/Si-MCM-41 | 652 | 0.90 |
| 3 | Co(25)/Pt(0.08)/Si-MCM-41 | 61 | 0.88 |
| 4 | Co(25)/Pt(0.05)/Si-MCM-41 | 77 | 0.90 |
| 5 | Co(25)/Ru(0.1)/Si-MCM-41 | 34 | 0.86 |
| 6 | Co(25)/Ru(0.1)/Si-MCM-41 | 245 | 0.91 |
| 7 | Co(25)/Ru(0.1)/Si-MCM-41 | 163 | 0.87 |
| 8 | Co(25)/Ru(0.1)/Si-MCM-41 | 244 | 0.91 |
| 9 | Co(16)/Si-MCM-41 | 163 | 0.86 |
| 10 | Co(16)/Al-MCM-41 | 214 | 0.86 |

While a preferred embodiment of the present invention has been shown and described, it will be understood that variations can be made to the preferred embodiment without departing from the scope of, and which are equivalent to, the present invention. For example, the structure and composition of the catalyst can be modified and the process steps can be varied.

The complete disclosures of all patents, patent documents, and publications cited herein are hereby incorporated herein by reference in their entirety. U.S. patent application Ser. No. 09/377,008, entitled Fischer-Tropsch Processes Using Xerogel and Aerogel Catalysts, filed concurrently herewith on Aug. 18, 1999, and U.S. patent application Ser. No. 09/377,077, entitled Fischer-Tropsch Processes Using Xerogel and Aerogel Catalysts by Destabilizing Aqueous Colloids, filed concurrently herewith on Aug. 18, 1999, are hereby incorporated herein by reference in their entirety.

U.S. patent application Ser. No. 09/314,921, entitled Fischer-Tropsch Processes and Catalysts Using Fluorided Supports, filed May 19, 1999, U.S. patent application Ser. No. 09/314,920, entitled Fischer-Tropsch Processes and Catalysts Using Fluorided Alumina Supports, filed May 19, 1999, and U.S. patent application Ser. No. 09/314,811, entitled Fischer-Tropsch Processes and Catalysts With Promoters, filed May 19, 1999, are hereby incorporated herein in their entirety.

The foregoing detailed description and examples have been given for clarity of understanding only. No unnecessary limitations are to be understood therefrom. The invention is not limited to the exact details shown and described, for variations obvious to one skilled in the art will be included within the invention by the claims.

What is claimed is:

1. A process for producing hydrocarbons, comprising contacting a feed stream comprising hydrogen and carbon monoxide with a catalyst in a reaction zone maintained at conversion-promoting conditions effective to produce an effluent stream comprising hydrocarbons, wherein the catalyst comprises at least one catalytic metal for Fischer-Tropsch reactions, and a non-layered mesoporous support which exhibits an X-ray diffraction after calcination that has at least one peak at a d-spacing of greater than 18 Ångstrom units.

2. The process of claim 1 wherein the catalyst comprises 10 to 30 percent by weight of a combination of cobalt and ruthenium, where the ruthenium content is from about 0.001 to about 1 percent by weight.

3. The process of claim 1 wherein the catalyst comprises 10 to 30 percent by weight of a combination of cobalt and rhenium, where the rhenium content is from about 0.001 to about 1 percent by weight.

4. The process of claim 1 wherein the catalyst comprises 10 to 30 percent by weight of a combination of cobalt and platinum, where the platinum content is from about 0.001 to about 1 percent by weight.

5. The process of claim 1 wherein the mesoporous support is Si-MCM-41.

6. The process of claim 1 wherein the mesoporous support is Al-MCM-41.

* * * * *